United States Patent [19]
Griffiths et al.

[11] Patent Number: 5,300,649
[45] Date of Patent: Apr. 5, 1994

[54] PROCESS FOR THE PRODUCTION OF LACTAMS

[75] Inventors: Gareth Griffiths, Visp; Felix Previdoli, Brig, both of Switzerland

[73] Assignee: Lonza Ltd., Gampel/Valais, Switzerland

[21] Appl. No.: 940,388

[22] Filed: Sep. 3, 1992

[30] Foreign Application Priority Data

Sep. 12, 1991 [CH] Switzerland ................... 2697

[51] Int. Cl.$^5$ ........................................... C07D 211/36
[52] U.S. Cl. ..................................... 546/290; 546/296
[58] Field of Search ............... 546/243, 216, 112, 290, 546/296

[56] References Cited

U.S. PATENT DOCUMENTS 3,737,457  6/1973  Cox et al. ........................... 260/545

FOREIGN PATENT DOCUMENTS 1930014 12/1969 Fed. Rep. of Germany.
533048  3/1993 Fed. Rep. of Germany.

OTHER PUBLICATIONS

Daluge et al., Journal of Organic Chemistry, vol. 43, No. 12, (1978) pp. 2311 to 2320.
Organic Synthesis, vol. 57 (1977), pp. 88 to 92.
Tetrahedron Letters, vol. 39, (1969) pp. 3351 and 3352.
Jagt et al., J. Org. Chem., 39, (1974), pp. 564 to 566.

Primary Examiner—Alan L. Rotman
Assistant Examiner—Raymond Covington
Attorney, Agent, or Firm—Fisher, Christen & Sabol

[57] ABSTRACT

$\beta,\gamma$-unsaturated $\delta$-lactams, especially 2-azabicyclo[2.2.1]hept-5-en-3-one, are produced by Diels-Alder reaction of 1,3-dienes with sulfonyl cyanides and subsequent hydrolysis. The sulfonyl cyanides were formed in situ from cyanogen chloride and the corresponding sulfinates. By the renewed reaction of the sulfinate formed in the hydrolysis of the Diels-Alder adducts with cyanogen chloride, the sulfonyl cyanides are regenerated and a catalytic cyclic process results. The 2-azabicyclo[2.2.1]hept-5-en-3-one is a starting compound in the synthesis of antiviral nucleoside analogs.

19 Claims, No Drawings

PROCESS FOR THE PRODUCTION OF LACTAMS

BACKGROUND OF THE INVENTION

1. Field Of The Invention

The invention relates to a process for the production of β,γ-unsaturated δ-lactams from 1,3-dienes and cyanogen chloride. The lactams produced according to the invention are represented by the general formula:

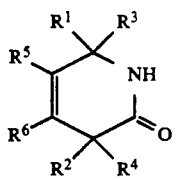

wherein $R^1$ and $R^2$ are either independent of one another and each is hydrogen, alkyl, aryl, alkoxy, aryloxy, alkylthio, arylthio or trialkylsilyloxy or together form a methanediyl or ethanediyl group, i.e., a $-(CH_2)_n-$ bridge wherein n is 1 to 2, $R^3$ and $R^4$ are independent of one another and each is hydrogen, alkyl, aryl, alkoxy, aryloxy, alkylthio, arylthio or trialkylsilyloxy and $R^5$ and $R^6$ are either independent of one another and each is hydrogen, alkyl, aryl, alkoxy, aryloxy, alkylthio, arylthio or trialkylsilyloxy or together with the two carbon atoms of the lactam ring connected by the double bond form a carbocyclic or heterocyclic ring having 5 to 8 ring members. An especially preferred product of the process according to the invention is 2-azabicyclo[2.2.1]hept-5-en-3-one, that represents the case where $R^1$, $R^2 = -CH_2-$ and $R^3 = R^4 = R^5 = R^6 = H$ of the general formula I.

2. Background Art

2-Azabicyclo[2.2.1]hept-5-en-3-one is a bicyclic lactam that is suitable as the initial material for the synthesis of carbocyclic nucleoside analogs [S. Daluqe and R. Vince, J. Org. Chem., 43, (1978), pages 2311 to 2320]. Such nucleoside analogs are of interest for their antiviral and chemotherapeutic properties as potential antitumoral agents. A known synthesis of 2-azabicyclo[2.2.1]hept-5-en-3-one is based on the Diels-Alder reaction of cyclopentadiene with p-toluene sulfonyl cyanide. In such case, a tosyl-azanorbornadiene first results that is converted by acid or alkaline hydrolysis into the target compound [J.C. Jaot and A.M. van Larsen, J. Org. Chem., 39. (1974), pages 564 to 566; S. Daluoe and R Vince, loc. cit.]. Drawbacks of such process are the explosiveness of p-toluene sulfonyl cyanide and the unfavorable quantitative ratio of the product to the waste product p-tolylsulfinyl-p-tolylsulfone. Moreover, the cyclopentadiene is used in great excess which must be distilled off before the hydrolysis.

BROAD DESCRIPTION OF THE IVNENTION

The main objective of the invention is to provide a process for the production of 2-azabicyclo[2.2.1]hept-5-en-3-one and other β,γ-unsaturated γ-lactams able to be produced with sulfonyl cyanides by Diels-Alder reaction of 1,3-dienes, which starts from easily available initial materials and yields no great amounts of by-products or waste products. Other objectives and advantages of the process of the invention are set out herein or are obvious herefrom to one skilled in the art.

The objectives and advantages of the invention are achieved by the process of the invention.

The invention involves a process for the production of lactams of the general formula:

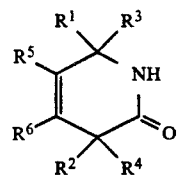

wherein $R^1$ and $R^2$ are either independent of one another and each is hydrogen, alkyl, aryl, alkoxy, aryloxy, alkylthio, arylthio or trialkylsilyloxy or together form a methanediyl or ethanediyl group, $R^3$ and $R^4$ are independent of one another and each is hydrogen, alkyl, aryl, alkoxy, aryloxy, alkylthio, arylthio or trialkylsilyloxy and $R^5$ and $R^6$ are either independent of one another and each is hydrogen, alkyl, aryl, alkoxy, aryloxy, alkylthio, arylthio or trialkylsilyloxy or together with the two carbon atoms of the lactam ring connected by the double bond form a carbocyclic or heterocyclic ring having 5 to 8 ring members. A 1,3-diene of the general formula:

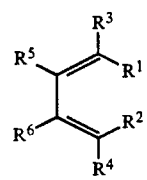

wherein $R^1$ to $R^6$ have the above-mentioned meanings, with cyanogen chloride in the presence of water and a sulfinic acid of the general formula:

$$R-SO_2H \qquad \qquad III$$

wherein R is a $C_1-C_6$-alkyl group or an optionally-substituted phenyl group, and/or a salt thereof, is subjected to a cycloaddition. Subsequently the cycloaddition intermediate is subjected to hydrolysis.

Preferably $R^3$ and $R^4$ are hydrogen. Preferably $R^5$ and $R^6$ are independent of one another and each is hydrogen or a $C_1-C_4$ alkyl group. Preferably $R^1$ and $R^2$ together form a methanediyl group. Preferably R is methyl, ethyl, phenyl, p-tolyl or p-bromophenyl. Preferably the sulfinic acid and/or the sulfinate is used in an amount of less than 0.5 mol, relative to 1 mol of 1,3-diene. Preferably the cycloaddition and the hydrolysis are each performed at a pH of 4 to 6. Preferably the pH is held constant during the cycloaddition and the hydrolysis by the addition of an alkali hydroxide. Preferably the cycloaddition and the hydrolysis are each performed in a solvent which is water, acetonitrile, tetrahydrofuran, dioxane, dichloromethane, toluene or a mixture of at least two of the solvents. Preferably the cycloaddition and the hydrolysis are each performed at a temperature of $-5°$ to $+25°$ C.

DETAILED DESCRIPTION OF THE INVENTION

It was surprisingly found that it is not only possible to produce a sulfonyl cyanide in situ from the corresponding sulfonyl chloride, a base, a reducing agent and cyanogen chloride and to cyclize with 1,3-diene, but that, after the cycloaddition, the alkanesulfinate or arenesulfinate resulting in the cleavage of alkylsulfonyl or arylsulfonyl groups is regenerated with additional cyanogen chloride under the same reaction conditions to sulfonyl cyanide and can be used again for cycloaddition. Thus, it is possible to get by with a catalytic amount of sulfonyl chloride or sulfonyl cyanide and to produce correspondingly little waste.

The basic cyclic process of the process according to the invention is illustrated by the following diagram:

(RSO₂Cl →)

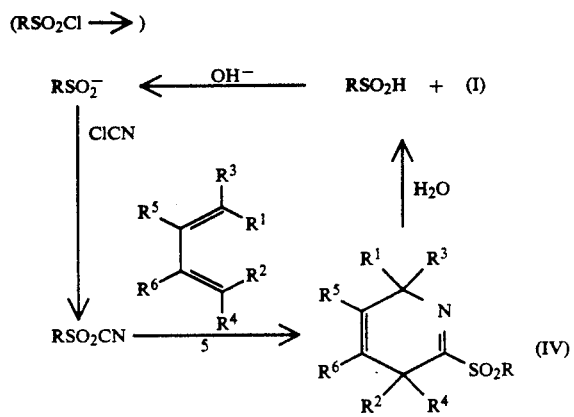

Thus, only the diene, cyanogen chloride and hydroxide ions corresponding to the idealized overall equation is used:

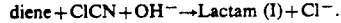

The entire reaction cycle including the reduction of sulfonyl chloride to the sulfinate necessary for forming the original amount of sulfonyl cyanide can be performed as a one-pot reaction. Of course, it is also within the scope of the invention to choose sulfinate or sulfonyl cyanide as such as the starting compound and to begin the reaction cycle at the corresponding point.

As dienes for the process according to the invention reactive electron-rich dienes are especially suitable. Such reactive electron-rich dienes are, for example, 1,3-cyclopentadiene, 1,3-cyclohexadiene, isoprene and 1,3-butadiene or dienes with electron-providing substituents, such as, alkyl groups, aryl groups, alkoxy groups, aryloxy groups, alkylthio groups, arylthio groups or trialkylsilyloxy groups. If the diene is sufficiently stable under the reaction conditions, such as, 1,3-cyclopentadiene, the entire diene amount can be introduced, otherwise it can be added corresponding to the reaction progress.

Suitable as the sulfonyl components are alkane- or arenesulfonic acid halides and pseudo halides, especially alkane- or arenesulfonic acid chlorides or cyanides, or alkane- or arenesulfinic acids or their salts. Preferably commercially obtainable ones, such as, methanesulfonyl- (mesyl-), ethanesulfonyl-, benzenesulfonyl-, p-toluenesulfonyl-(tosyl-), or p-bromobenzenesulfonyl-(brosyl-) -chloride or -cyanide, are used. Preferably the sulfonyl component is used in an amount of less than 0.5 mol, relative to 1 mol of the diene. Amounts of 0.2 mol and less are especially preferred.

The cycloaddition is suitably performed in a neutral to moderately acid environment, advantageously at a pH of 2 to 7, preferably in a weak acid environment at a pH of 4 to 6. Under these conditions both the hydrolysis of the Diels-Alder adduct (IV) to lactam (I) and the reformation of the sulfonyl cyanide to the sulfinate occur so that the catalytic cycle is closed.

Since hydrogen chloride results in the reaction, the pH must be held constant by the addition of a base, unless a buffered system is used. As the base, both organic bases, such as, quaternary ammonium hydroxides, and inorganic bases, such as, alkali or alkaline earth hydroxides, are suitable. Preferably an alkali hydroxide is used as the base, sodium hydroxide is especially preferred. The base addition takes place preferably by means of a suitable control device, composed of a pH-meter and a gauge controlled by the former.

As the solvent, suitably a solvent is used that either is inert to the compounds occurring in the reaction cycle, or at most slowly reacts with them. Such solvents include, for example, water, acetonitrile, tetrahydrofuran, dioxane, dichloromethane, toluene, or mixtures or two-phase systems composed of at least two of these solvents. Preferably the cycloaddition is performed in an aqueous solvent mixture or in a vigorously stirred two-phase system of water and a water-immiscible organic solvent. Tetrahydrofuran and the water/dichloromethane system are especially preferred.

The cycloaddition is preferably performed at a temperature of −5° to +25° C., especially preferred at +5° to +20° C.

The working-up of the reaction mixture can take place in a way known in the art, for example, by extraction with a solvent of low polarity.

The following examples illustrate the performance of the process according to the invention.

Example 1

2-Azabicyclo[2.2.1]hept-5-en-3-one 19.5 g (0.17 mol) of methanesulfonyl chloride was instilled within 30 minutes at 18° to 20° C. in a solution of 21.4 g (0.17 mol) of sodium sulfite and 28.6 g (0.34 mol) of sodium bicarbonate in 330 ml of water. The mixture was left standing overnight and then cooled to 15° C. To the thus-produced sodium methanesulfinate solution, 88.1 g (1.33 mol) of freshly distilled cyclopentadiene and 83 ml of dichloromethane were added and 116.9 g (1.90 mol) of cyanogen chloride was introduced at 15° C. within 5 hours under stirring. By a control device composed of a pH-meter and a pulse controlled metering device, the pH was held constant at 5 by adding a total of about 224 g of 30 percent sodium hydroxide solution altogether during the introduction and then for another 1.75 hours. Then the pH was adjusted to 8 by the addition of 10.4 g of 30 percent sodium hydroxide solution and the reaction mixture was extracted 4 times with 290 ml of dichloromethane each. The combined organic phases were dried on magnesium sulfate, filtered and concentrated by evaporation in a vacuum. The residue was dried in a high vacuum. The yield was 103.0 g of orange crude product, having a content (HPLC) of 95.5 percent.

Example 2

2-Azabicyclo[2.2.1]hept-5-en-3-one 45.9 g (0.25 mol) of sodium-4-toluenesulfinate (hydrate) was dissolved in 300 ml of water and cooled to 0° C. 82.6 g (1.25 mol) of cyclopentadiene (freshly distilled), 100 ml of tetrahydrofuran and 15.0 g (0.25 mol) of acetic acid were added to this solution and the mixture was cooled to −3° to +1° C. At this temperature 78.0 g (1.27 mol) of cyanogen chloride was introduced within 80 minutes and the mixture was then stirred at 10° C. Analogously to Example 1, the pH was kept at 4 over a period of 6 hours by adding a total of about 120 g of 30 percent sodium hydroxide solution. Then the pH was raised to 8 by the addition of another 69 g of 30 percent sodium hydroxide solution. The mixture was mixed with 300 ml of dichloromethane and 100 ml of water; the phases were separated; and the aqueous phase was extracted twice with 150 ml of dichloromethane each. The combined organic phases were dried on magnesium sulfate and filtered. The solvent was distilled off in a vacuum and the residue dried in a high vacuum. The yield was 80.3 g of yellowish-brown crude product, having a content (HPLC) of 78.7 percent.

What is claimed is:

1. Process for theproduction of lactams of the fomrula:

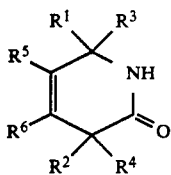

I wherein R¹ and R² are either independent of one another and each is hydrogen, alkyl, aryl, alkoxy, aryloxy, alkylthio, arhlthio or trialkylsiloyloxy or together from a methanediyl or ethanediyl group, R³ and R⁴ are independent of one another and each is hydrogen, alkyl, aryl, alkoxy, aryloxy, alkylthio, arylthio or trialkylsilyloxy and R⁵ and R⁶ are either independent of one another and each is hydrogen, alkyl, aryl, alkoxy, aryloxy, alkylthio, arylthio or trialkylsilyloxy or together with the two carbon atoms of the lctam ring conncted by thedfouble bond form a carbocyclic or heterocyclic ring having 5to 8 ring members, comprising subjecting a 1,3-diene of the general formula:

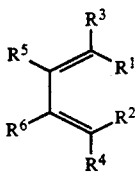

II wherein R¹ to R⁶ have the above-mentioned meanings, in thepresence of water to a cyclo-addition with a sulfonyl cyanide, said sulfonyl cyanide at least partly being formed in situ from a sulfinic acid of the fomrula:

III wherein R is a C₁-C₆-alkyl group or an optionally substituted phenyl group, and/or a salt of thereof, and cyanogen chloride and in the same process step subjectin the cycloaddition inermediate to hydrolysis with said water.

2. The process according to claim 1 wherein R³ and R⁴ are hydrogen.

3. The process according to claim 2 wherein R⁵ and R⁶ are independent of one another and each is hydrogen or a C₁-C₄-alkyl group.

4. The process according to claim 3 wherein R¹ and R² together form a methanediyl group.

5. The process according o claim 4 wherein R is selected from the group consisting of methyl, ethyl, penyl, p-tolyl and p-bromophenyl.

6. The process according to claim 5 wherein the sulfinic acid and/or the sulfinate is used in an amount of less than 0.5 mol, relative to 1 mol of.1,3-diene.

7. The process according to claim 6 wherein the cycloaddition and the hydrolysis are each performed at a pH of 4 to 6.

8. The process according to claim 7 wherein the pH is held constant during the cycloaddition and the hydrolysis by addition of an alkali hydroxide.

9. The process according to claim 8 wherein the cycloaddition and the hydrolysis are each performed in a solvent from the group consisting of water, acetonitrile, tetrahydrofuran, dioxane, dichloromethane, toluene and a mixture of at least two of said solvents.

10. The process according to claim 9 wherein the cycloaddition and the hydrolysis are each performed at a temperature of −5° to +25° C.

11. The process according to claim 1 wherein R⁵ and R⁶ are independent of one another and each is hydrogen or a C₁-C₄-alkyl group.

12. The process according to claim 1 wherein R¹ and R² together form a methanediyl group.

13. The process according to claim 1 wherein R is selected from the group consisting of methyl, ethyl, phenyl, p-tolyl and p-bromophenyl.

14. The process according to claim 1 wherein the sulfinic acid and/or the sulfinate is used in an amount of less than 0.5 mol, relative to 1 mol of 1,3-diene.

15. The process according to claim 1 wherein the cycloaddition and the hydrolysis are each performed at a pH of 4 to 6.

16. The process according to claim 1 wherein the pH is held constant during the cycloaddition and the hydrolysis by addition of an alkali hydroxide.

17. The process according to claim 1 wherein the cycloaddition and the hydrolysis are each performed in a solvent from the group consisting of water, acetonitrile, tetrahydrofuran, dioxane, dichloromethane, toluene and a mixture of at least two of said solvents.

18. The process according to claim 1 wherein the cycloaddition and the hydrolysis are each performed at a temperature of −5° to +25° C.

19. The process according to claim 1 wherein the sulfinic acid genrated by the hydrolysis step is treated with a base, and regenerated in situ with cyanogen chloride to sulfonyl cyanide.

* * * * *